United States Patent [19]

Tanaka et al.

[11] Patent Number: 5,022,980
[45] Date of Patent: Jun. 11, 1991

[54] SYSTEM FOR DETERMINING CONCENTRATION OF AN ELECTROLYTE

[75] Inventors: Akiko Tanaka; Toshio Takiguchi, both of Otawara, Japan

[73] Assignee: Kabushiki Kaisha Toshiba, Kawasaki, Japan

[21] Appl. No.: 292,333

[22] Filed: Dec. 30, 1988

[51] Int. Cl.⁵ .................. G01N 27/26; G01N 27/414
[52] U.S. Cl. ............................ 204/400; 73/1 R; 204/153.1; 204/401; 204/416; 340/501; 364/497
[58] Field of Search ............... 204/401, 1 T, 416, 418, 204/419, 400, 153.1; 73/1 R; 364/497; 340/501

[56] References Cited

U.S. PATENT DOCUMENTS

| | | | |
|---|---|---|---|
| 4,218,746 | 8/1980 | Koshiishi | 364/571 |
| 4,654,127 | 3/1987 | Baker et al. | 204/1 T |
| 4,786,394 | 11/1988 | Enzer et al. | 204/401 |

FOREIGN PATENT DOCUMENTS 2937227 12/1980 Fed. Rep. of Germany .
211353 10/1985 Japan .

*Primary Examiner*—T. Tung
*Attorney, Agent, or Firm*—Oblon, Spivak, McClelland, Maier & Neustadt

[57] ABSTRACT

A system and method for checking the concentration of an electrolyte in a solution utilizing ion-selective electrodes for sequentially measuring potential levels of a sample solution and a correction solution at selected time intervals. The potential levels of the positive and negative ions in the sample and corrective solutions are then compared with a standard potential level for the correction solution. A procedure determines if an abnormal deviation in the sample solution exists and if this abnormal deviation is caused by the actual concentration of electrolytes in the sample solution or if the abnormality is caused by an error in measurement. An alarm is sounded to indicate that the abnormality exists and the cause of the abnormality.

8 Claims, 4 Drawing Sheets

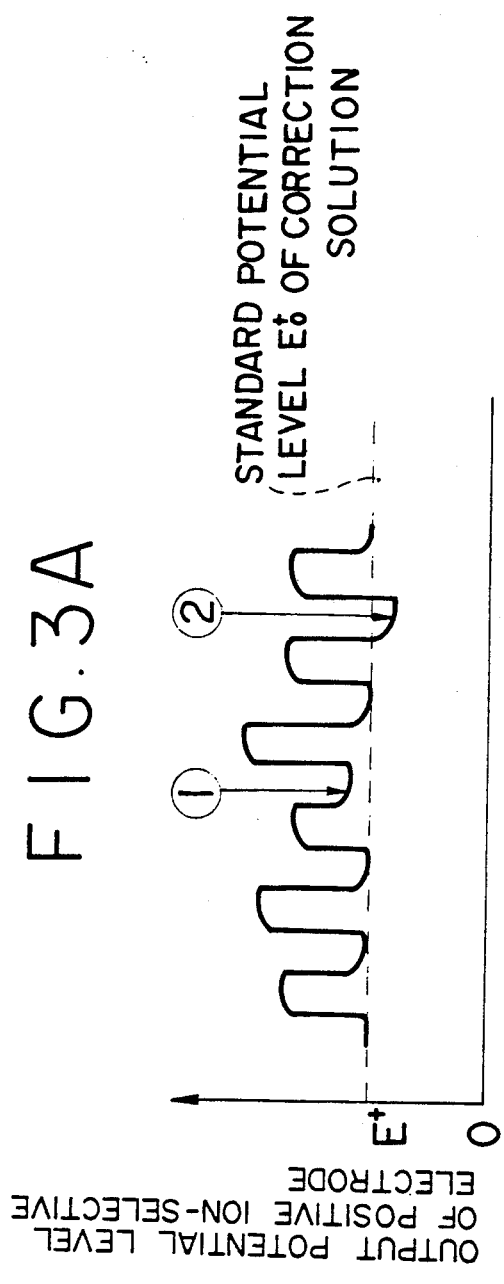
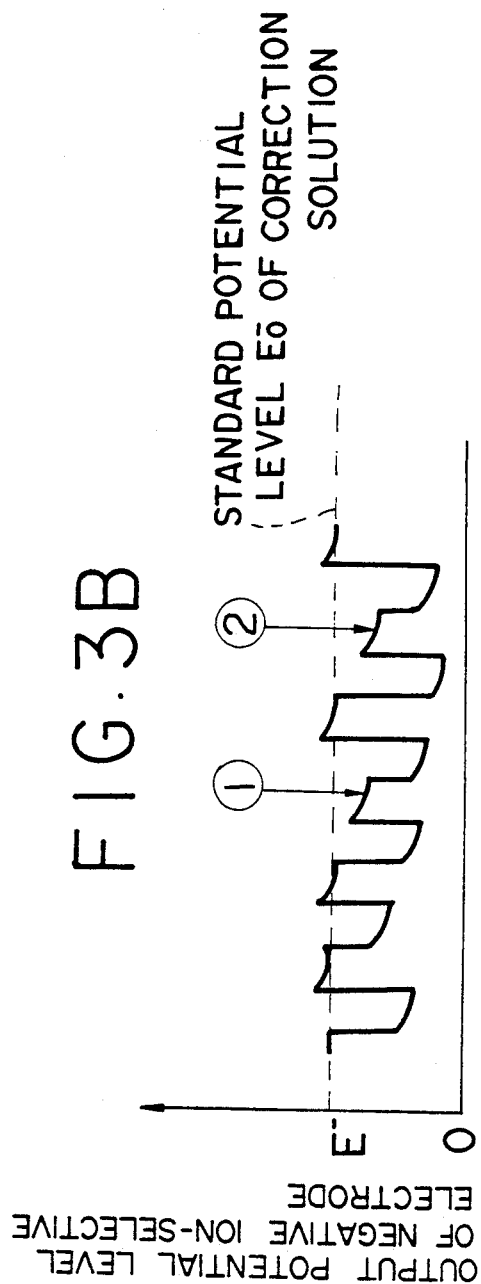

SYSTEM FOR DETERMINING CONCENTRATION OF AN ELECTROLYTE

BACKGROUND OF THE INVENTION

1. Field of the Invention

This invention relates to a system and procedures therewith for determining concentration of electrolytes in the field of medical examination.

2. Description of the Prior Art

In the medical examination field, ions in the human blood, urine, and so on, in particular, positive ions such as sodium ion (Na+) and potassium ion (K+), and negative ions such as chloride (Cl−) ion are determined, and the obtained data is useful as diagnostic information. For the determination of ionic concentrations, an ion-selective electrode unit can be used comprising at least one negative electrode responsive to positive ions and/or at least one positive electrode responsive to negative ions and a reference electrode.

Once a sample of a test solution (this term refers hereinafter to a solution containing an electrolyte of which an ionic concentration is to be measured) such as blood is placed in such an ion-selective electrode unit, a positive or negative ion activates the corresponding negative or positive electrode to produce an electromotive force in accordance with the concentration of it between an activated electrode and the reference electrode.

When ionic concentration is determined as described above, the ion-selective electrode unit may permit the electromotive force generated by it to drift with the course of time. In order to avoid the unwanted influence and thus to make accurate determination, typically the ionic concentration of a test solution is determined with respect to a correction solution having substantially the same composition as the test solution. The potential level of the correction solution is measured before or after the ionic concentration measurement of the test solution, and thus the ionic concentration of the test solution is obtained as the difference of the measured potential level of the test solution from the measured potential level of the correction solution.

Correction solution for use in correcting the determination of ionic concentration of a test solution should be prepared or composed to have an always constant potential level Eo under normal conditions, and the ionic concentration of a test solution such as sample 1, 2 or 3 is determined in accordance with the difference in potential level from Eo as shown in FIG. 5. Eo may be measured before or after determination of the ionic concentration of a test solution, preferably alternately in measurement of test and correction solutions possibly with effective results.

There is a problem encountered in the determination of the concentration of electrolytes in the prior art if the potential level of correction solution, which originally should remain constant, varies for some cause, ionic concentration of test solution can be determined with error, due to the variation, resulting in an inaccurate value.

FIG. 6 shows where Eo deviates by $\Delta E$ for some cause between determinations with test solution samples 1 and 2. As a result, $E_2$ is not obtained but $E_2'$ is obtained instead. Thus an error results.

OBJECTS AND SUMMARY OF THE INVENTION

The present invention has been accomplished to solve the problem above-stated.

It therefore is the principal object of the present invention to provide a system and procedures therewith for determining the concentration of an electrolyte and which are capable of detecting a variation in the potential level of a correction solution if such a variation occurs.

The first invention for achieving the above-mentioned object is a system comprising an ion-selective electrode unit for measuring the potential level of a test or correction solution, a memory for storing the measured potential levels of the correction solution, and means for comparing two potential levels of the correction solution, and outputting an alarm signal if variation or abnormality has been detected.

The second invention for achieving the above-mentioned object is a procedure comprising (a) a first step of measuring and storing the potential level of the correction solution in a normal state (referred to as standard potential level of correction solution, hereinafter); (b) a second step of comparing, with respect to the correction solution, potential levels measured at time intervals with the standard potential level; and (c) a third step of outputting an alarm signal if variation in potential level is detected in the preceding step (b).

The third invention for achieving the above-mentioned object is another procedure comprising (a) a first step of measuring positive and negative standard potential levels of correction solution and storing the obtained data; (b) a second step of comparing, with respect to the correction solution, positive and negative potential levels measured at time intervals with the standard positive and negative potential levels, respectively; (c) a third step of discrimanating a variation pattern, i.e. whether positive or negative potential levels deviate towards the opposite or same polarity to or as each other; (d) a fourth step of outputting the result of discrimination; (e) a fifth step of signaling information of cause therefor probable from the result of discrimination; and (f) a sixth step of signaling information of countermeasure to be taken by an operator against the probable cause. The term "positive potential level" refers to output potential level of positive ion-selective electrode(s), and the term "negative potential level" refers to output potential level of negative ion-selective electrode(s), in this specification.

According to the first invention, the standard positive and/or negative potential level of correction solution are measured and stored, and thus the comparison between the stored standard potential level and a measured potential level can detect variation in potential level of the correction solution when abnormal.

According to the second invention, either a standard positive or negative potential level of correction solution is measured and stored with which potential levels of the same polarity measured at time intervals are compared, and thus if variation in a potential level of the polarity is detected, an alarm signal can be output.

According to the third invention, both standard positive and negative potential levels are measured and stored on a memory. With them, positive and negative potential levels measured at time intervals are compared, and thus if variation in positive and/or negative potential level, i.e. abnormal state of the correction solution is detected, an alarm signal can be output.

BRIEF DESCRIPTION OF THE DRAWINGS

FIGS. 3A and 3B are waveforms of potential level illustrative of the principle of measurement with the system of FIG. 1;

DESCRIPTION OF THE PREFERRED EMBODIMENTS

Figure 1:
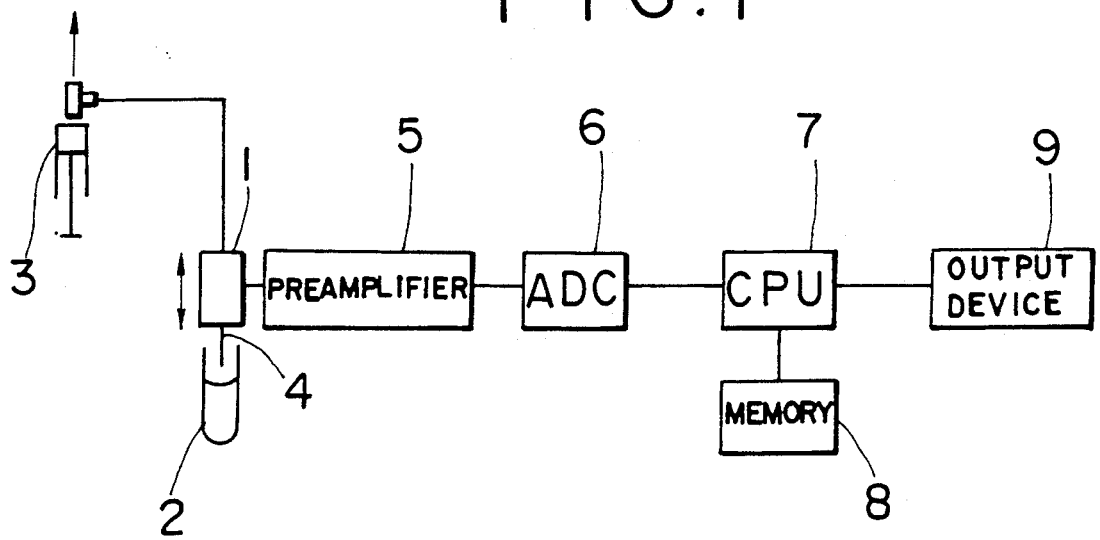
FIG. 1 is a block diagram of an illustrative embodiment of a system for measuring concentration of electrolyte according to the first invention.

The first invention shown in FIG. 1 is illustrative of the construction of a system for the concentration of an electrolyte. A reference numeral 1 designates an ion-selective electrode unit for measuring the potential level of a sample (solution to be measured: test solution or correction solution) in a reaction tube 2, and the obtained results are used for the determination of ionic concentration. Reference numeral 3 indicates a suction pump for sucking a sample in the reaction tube 2 and delivering the sample through a suction nozzle 4 into the ion-selective electrode unit 1.

Figure 2:
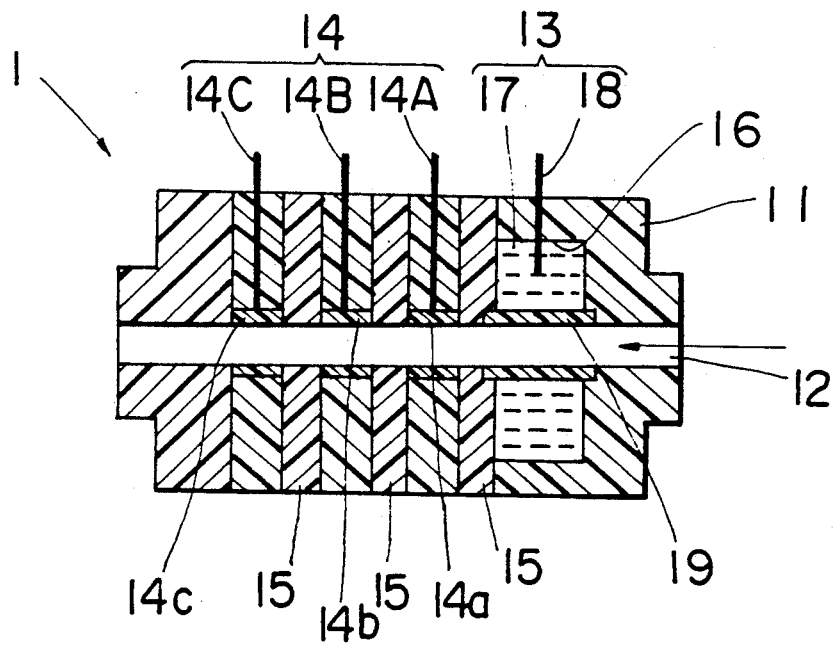
FIG. 2 is an longitudinal sectional view of an ion-selective electrode unit as an constructive element for the system of FIG. 1.

FIG. 2 illustrates an example of ion-selective electrode unit 1 which comprises an insulating body 11 including a passageway 12 for feeding a sample, and is provided in the surrounding with a reference electrode 13 and a plurality of ion-selective electrodes 14 such as 14A, 14B and 14C having an inductive layer $14a$, $14b$ and $14c$ at respective end portions in contact with the sample and sensitive to $Na^+$, $K^+$ and $Cl^-$, respectively. The electrodes 14A, 14B and 14C are insulated with insulating spacers 15 from each other. The body 11 of insulating material is provided with a recess 16 filled therein with a solution 17 such as electrolyte of sodium chloride (NaCl). A conductor 18 projects into the solution 16 in the recess 17, which communicates through a liquid communication 19 to the sample. When a solution to be measured flows through the liquid passageway 12, electrodes 14A, 14B and 14C respond to $Na^+$, $K^+$ and $Cl^-$, respectively, and thus potential levels in accordance with concentrations of ions can be measured between the ion-selective electrodes $14a$, 14B and 14C, respectively, and the reference electrode 13.

When a potential level of the sample is measured by the ion-selective electrode unit 1, the measured potential level E is expressed by the Nernst equation:

$$E = Eo + \frac{RT}{nF} \log_e C \qquad (1)$$

wherein characters are as follows: Eo, constant dependent on electrode material; R, gas constant; T, absolute temperature, F, Faraday's constant; n, the number of signed ions); and C, ionic concentration to be measured.

As self-evident, from equation (1) in which Eo, R, T, n and F are each constant, ionic concentration C can be obtained by the measurement of potential level E.

Potential level E is measured as a higher value with increasing ionic concentration of sample when $n>0$, i.e. for the determination of positive ionic concentration, and as a lower value with increasing ionic concentration of sample when $n<0$, i.e., for the determination of negative ionic concentration.

In general, a sample solution, whether sample or correction solution, is about 10 times diluted and then placed into the ion-selective electrode unit 1 probably because of reduced sampling particularly of precious material, and because of apparently much declined influence of substances remaining undissolved such as protein on the measurement.

Potential level or electromotive force measured by the ion-selective electrode unit 1 is amplified at a preamplifier 5, converted into digital signal by A-D converter 6 and stored on a memory 8 under the control of a central processing unit (CPU) 7.

The positive potential level of a correction solution in normal state is measured in the positive ion-selective electrode unit 1 and stored as the standard positive potential level $E_o^+$ shown in FIG. 3A so as to remain constant, on the memory 8. Likewise the negative potential level of the correction solution in normal state is measured in the negative ion-selective electrode unit 1 and stored as the standard negative potential level $E_o^-$ shown in FIG. 3B so as to remain constant, on the memory 8.

In addition to the standard positive and negative potential levels, on the memory 8, positive and negative potential levels of the correction solution, $E^+$'s and $E^-$'s, respectively, and positive and negative potential levels of test solution measured at time intervals are stored.

CPU 7 functions to compare every measured $E^+$ with $E_o^+$ and every measured $E^-$ with $E_o^-$, and each obtained result or variation is compared with the respective preset threshold value $\Delta Et$. When the corresponding equation Positive potential: $|E^+ - E_o^+| \leq \Delta Et$ (2)

or

Negative potential: $|E^- - E_o^-| \leq \Delta Et$ (3)

is met, judgment is taken as normal and otherwise as abnormal. The threshold values are set in accordance with resolving power, for instance, to 0.1 mV. The judgment is signaled to an output device 9 such as CRT display or printer.

When variation in the positive and negative potential levels of correction solution $E^+$ and $E^-$ measured by the ion-selective electrode unit 1 at time intervals has been found, the cause for this can be understood by identifying the pattern of the variation. Such variation falls into two patterns in accordance with the relative relationship between deviations in $E^+$ and $E^-$ from $E_o^+$ and $E_o^-$, respectively: one (pattern 1) in which positive and negative potential levels $E^+$ and $E^-$ become deviated towards opposite polarity with respect of each other as indicated at "1" in FIGS. 3A and 3B, respectively, and the other (pattern 2) in which $E^+$ and $E^-$ become deviated towards the same polarity with respect to each other as indicated at "2" in FIGS. 3A and 3B, respectively. Pattern 1 means phenomenon which is in accordance with the above-mentioned Nernst equation and hence leads to an inference that the abnormal variation may be due to sample. On the other hand, pattern 2 means phenomenon which does not meet the Nernst equation and hence leads to the inference that the variation is not due to sample but to the measuring system. In view of this, patterns 1 and 2 should be previously stored in memory through CPU 7, by reference to which, if variation is detected, which pattern the variation has is output, whereby what the cause is can be understood.

In the following, the measuring procedure according to the second invention with the measuring system according to the first invention will be described.

Now with a sample containing, for example, positive ions, as either positive or negative ions may be selected, measurement is carried out as follows: Standard positive potential level $E_o$ of the correction solution previously measured is stored on the memory 8. Positive potential levels of the correction solution $E^+$ are measured at time intervals. By the function of CPU 7, each obtained potential level $E^+$ is compared with the standard potential level $E_o^+$, and if the condition under equation (2) is not met, the alarm is signaled to an output device 9, whereby an operator can notice abnormality and probable cause therefor, and take appropriate countermeasure. Measurement with a sample containing negative ions is carried out in the same way except that if the condition under equation (3) is not fulfilled, an alarm signal is output.

Figure 4:
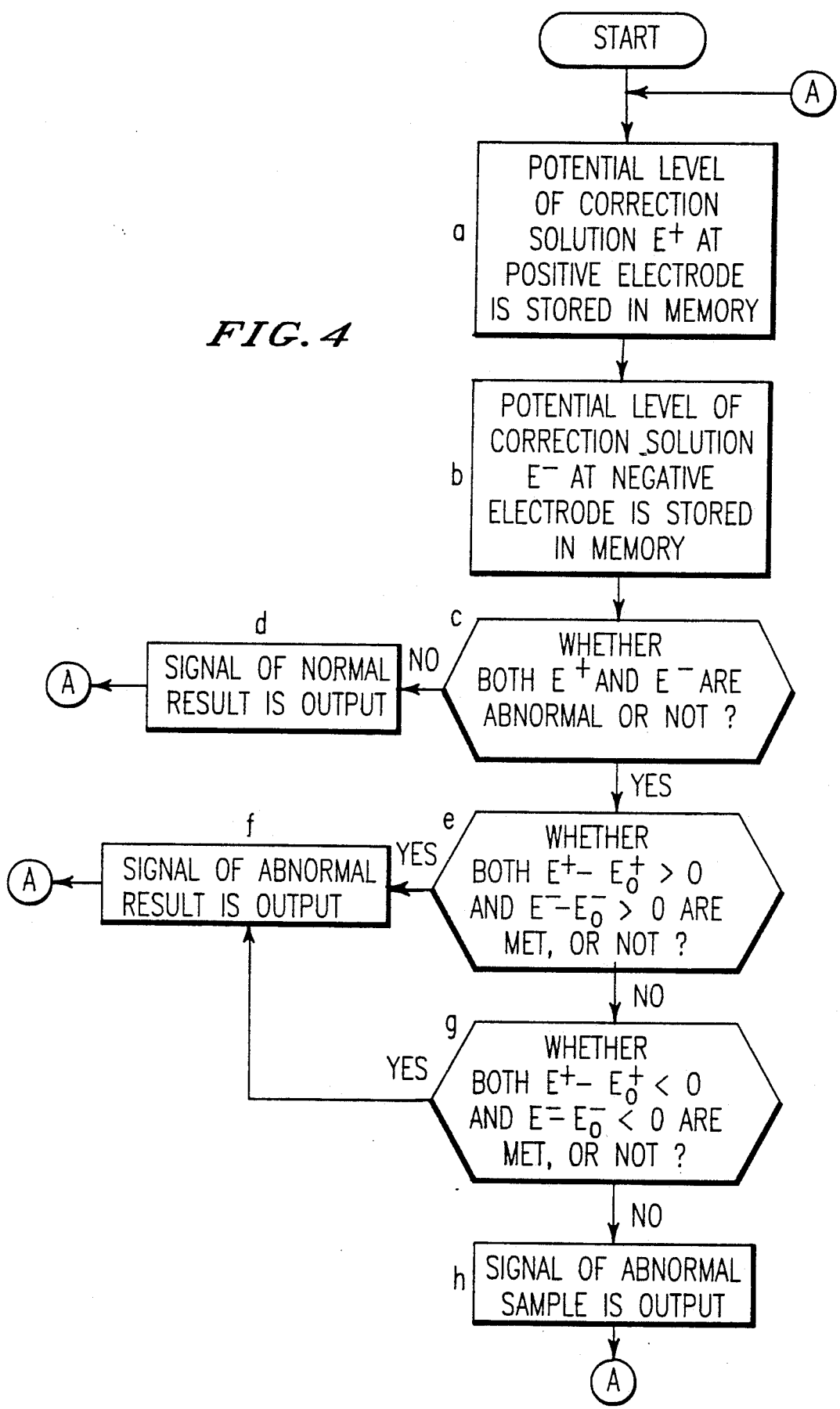
FIG. 4 is a flowchart illustrative of a procedure of measurement with the system of FIG. 1.
Figure 5:
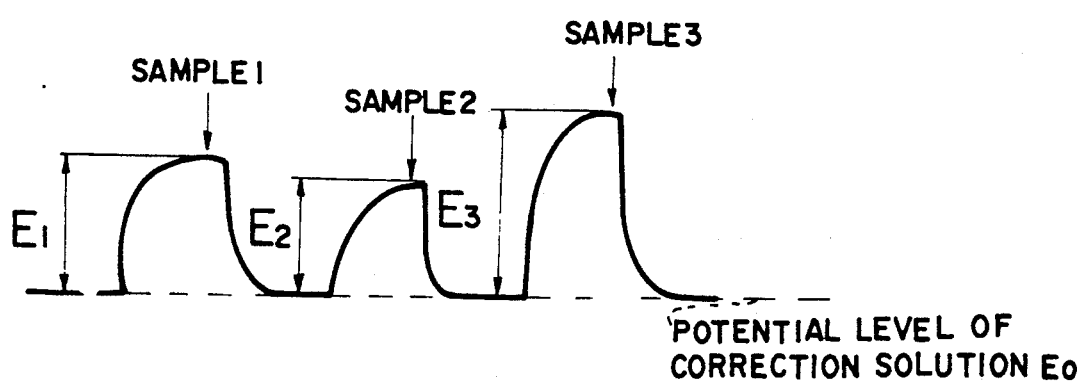
FIGS. 5 and 6 are waveforms illustrative of the principle of measuring ionic concentration, respectively.
Figure 6:
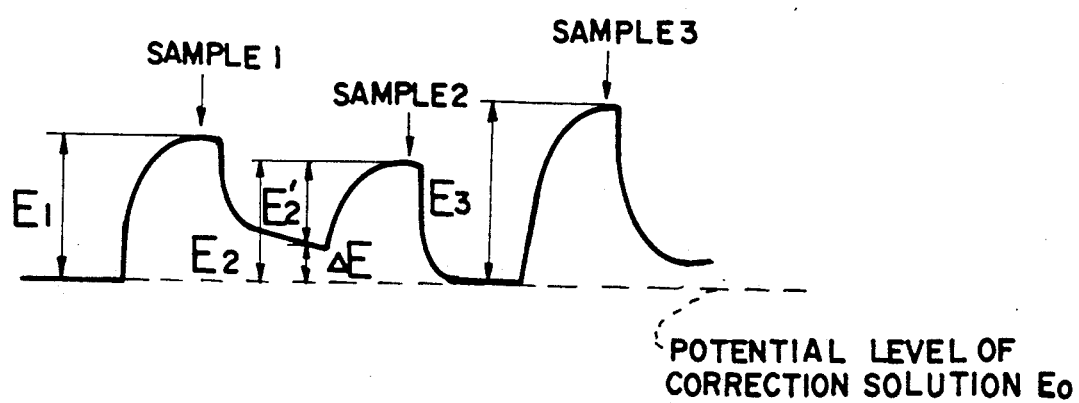

Now the measuring procedure according to the third invention with the system according to the first invention will be described with reference to the flow chart shown in FIG. 4.

The standard positive and negative potential levels, $E_o^+$ and $E_o^-$, are previously measured and stored on the memory 8. Measurement with the correction solution is carried out at time intervals: in steps "a" and "b", positive and negative potential levels, $E^+$ and $E^-$, respectively, are measured and stored on the memory 8. In step "c", judgment whether $E^+$ and $E^-$ are normal or abnormal is made depending on whether equations (2) and (3) are met, respectively. If the answer is no, then control is transferred to step "d" at which a signal of "normal" is output. If the answer is yes, then control is transferred to step "e" at which judgment whether both "$E^+$ and $E^-$" deviate towards positive polarity, which is one condition of the pattern 2, or not, is made. If the answer is yes, then control is transferred to step "f" where signal that the measuring system is abnormal is output. If no, control is transferred to step "g" where the other condition of the pattern 2: judgment whether both "$E^+$ and $E^-$" deviate towards negative polarity, is made. If yes, control is transferred to step "f". In brief, whether the conditions of pattern 2 are met, or not, are judged in steps "e" and "g", if the answer are yes in either step, then control is transferred to step f, and this leads to the inference that abnormal variation is due to the measuring system.

On the other hand, if the answer at step "g" is no, then the condition of pattern 1 becomes met, and thus control is transferred to step "h" where a signal that the sample solution or washing-drying device is abnormal is output.

The measuring procedure according to the third invention has advantages over the measuring procedure according to the second invention that when a measured result with correction solution sample is detected to be abnormal, alarm signal is output, which includes information having identified whether correction solution sample or the measuring system is cause for the abnormal deviation. An operator therefore can investigate the cause for abnormal variation and thus take a countermeasure early.

As described above, when the potential level of correction solution is abnormally varied, a signal of abnormal variation can be output (according to the second and third inventions) and the cause for it can be identified by the reference to previously-stored variation patterns (according to the third invention), and thus accurate determination of ionic concentration of the test solution is possible.

What is claimed is:

1. A system for determining the concentration of an electrolyte in a solution by measuring the difference between potential levels of the solution containing the electrolyte and a corresponding correction solution, comprising:

ion-selective electrode means responsive to positive and negative ions for sequentially measuring positive and negative potential levels of positive and negative ions in a sample solution and in the correction solution to provide sample data of positive and negative potential levels;

comparing means for comparing at time intervals said positive and negative potential levels of the correction solution and the sample solution with standard potential levels for the correction solution so as to detect any variation;

discriminating means for discriminating which of two variation patterns said any variation indicates;

means for detecting an abnormal variation between the positive and negative potential levels of said sample solution and said correction solution and said standard potential levels of said correction solution; and means for determining if said abnormal variation is due to said sample solution or due to an error in measurement.

2. A system according to claim 1, further comprising:
   alarm sounding means for indicating that the abnormal variation exists.

3. A system according to claim 2, wherein:
   the alarm sounding means sounds one alarm when the abnormal variation is due to the sample solution and sounds another alarm when the abnormal variation is due to an error in measurement.

4. A system for determining the concentration of an electrolyte in a solution utilizing a measuring system, the system comprising the steps of:

means for obtaining a test solution having an electrolyte concentration to be measured;

means for measuring positive and negative potential levels of a correction solution having substantially a same composition as the test solution in a normal state for use as standard positive and negative potential levels of the correction solution;

means for storing the standard positive and negative potential levels of the correction solution;

means for measuring positive and negative potential levels of the test solution and the correction solution at time intervals;

means for comparing each measured positive and negative potential level of the test and the correction solutions respectively with the standard positive and negative potential levels of the correction solution;

means for detecting if a variation exists between the standard and measured positive and negative levels of the correction solution;

means for determining whether the positive and negative potential levels of the correction solution measured at time intervals deviate towards one of an opposite polarity with respect to each other and a same polarity with respect to each other.

means for obtaining the concentration of the electrolyte of the test solution as a difference between potential levels of the test solution containing the electrolyte to be measured with the measured potential levels of the correction solution when no variation is detected; and means for outputting a signal of abnormal results when a variation is detected.

5. A system according to claim 4, wherein the outputting means further comprises:

means for outputting a signal indicating an abnormal measuring system when the positive and negative levels of the correction solution deviate towards the same polarity with respect to each other.

6. A system according to claim 5, wherein the outputting means further comprises:

means for outputting a signal indicating an abnormal sample when the positive and negative levels of the correction solution deviate towards the opposite polarity with respect to each other.

7. A system according to claim 6, wherein the outputting means further comprises:

means for outputting a signal indicating an abnormal measuring system when the positive and negative levels of the correction solution deviate towards the same polarity with respect to each other.

8. A system according to claim 4, wherein the variation of the detecting step is greater than a predetermined value.

* * * * *